US006355798B1

(12) United States Patent
Madin et al.

(10) Patent No.: US 6,355,798 B1
(45) Date of Patent: Mar. 12, 2002

(54) TRIAZOLO-PYRIDAZINE DERIVATIVES AS LIGANDS FOR GABA RECEPTORS

(75) Inventors: Andrew Madin, Sawbridgeworth; Andrew Pate Owens, Huntingdon, both of (GB)

(73) Assignee: Merck Sharp & Dohme Ltd., Hoddesdon (GB)

( * ) Notice: Subject to any disclaimer, the term of this patent is extended or adjusted under 35 U.S.C. 154(b) by 0 days.

(21) Appl. No.: 09/582,376

(22) PCT Filed: Jan. 13, 1999

(86) PCT No.: PCT/GB99/00105

§ 371 Date: Jun. 22, 2000

§ 102(e) Date: Jun. 22, 2000

(87) PCT Pub. No.: WO99/37645

PCT Pub. Date: Jul. 29, 1999

(30) Foreign Application Priority Data

Jan. 21, 1998 (GB) .............................................. 9801208

(51) Int. Cl.[7] .................. C07D 487/00; A61K 31/495; A61K 31/5025
(52) U.S. Cl. ................... 544/236; 514/252.06
(58) Field of Search ...................... 544/236; 514/252.06

(56) References Cited

U.S. PATENT DOCUMENTS

| 4,112,095 A | | 9/1978 | Allen, Jr. et al. ............ 424/250 |
|---|---|---|---|
| 4,117,130 A | | 9/1978 | Allen, Jr. et al. ............ 424/250 |
| 4,230,705 A | | 10/1980 | Allen, Jr. et al. ............ 424/250 |
| 4,260,755 A | | 4/1981 | Moran et al. ................ 544/236 |
| 4,260,756 A | * | 4/1981 | Moran et al. ................ 544/236 |
| 4,578,464 A | * | 3/1986 | Cregge et al. ......... 514/252.06 |
| 4,654,343 A | | 3/1987 | Albright et al. ............ 514/248 |

FOREIGN PATENT DOCUMENTS

| DE | 27 41 763 | 9/1977 |
|---|---|---|
| EP | 0 085 840 | 8/1983 |
| EP | 0 134 946 | 3/1985 |
| GB | 1 589 237 | 5/1991 |
| WO | WO 98/04559 | 2/1998 |

OTHER PUBLICATIONS

Bayley, et al., J. Psychopharmacol., 10: 206–213 (1996).
Bristow, et al., J. Pharmacol. Exp. Ther., 279: 492–501 (1996).
Dawson, et al., Psychopharmacology, 121: 109–117 (1995).
Wafford, et al., Mol. Pharmacol., 50: 670–678 (1996).

* cited by examiner

Primary Examiner—Mukund J. Shah
Assistant Examiner—Slidhaker B. Patel
(74) Attorney, Agent, or Firm—Shu Muk Lee; David L. Rose

(57) ABSTRACT

1,2,4-triazolo[4,3-b]pyridazine derivatives, possessing an optionally substituted cycloalkyl, phenyl or heteroaryl substituent as the 3-position and an amino moiety at the 6-position, are selective ligands for $GABA_A$ receptors, in particular having high affinity for the α2 and/or α3 subunit thereof, are useful in the treatment of anxiety and convulsions.

8 Claims, No Drawings

TRIAZOLO-PYRIDAZINE DERIVATIVES AS LIGANDS FOR GABA RECEPTORS

This is an application under 35 U.S.C. 371 of PCT/GB99/00105 and claims priority from Great Britain Application No.9801208.1, filed Jan. 21,1998.

The present invention relates to a class of substituted triazolo-pyridazine derivatives and to their use in therapy. More particularly, this invention is concerned with substituted 1,2,4-triazolo[4,3]pyridazine derivatives which are ligands for $GABA_A$ receptors and are therefore useful in the therapy of deleterious mental states.

Receptors for the major inhibitory neurotransmitter, gamma-aminobutyric acid (GABA), are divided into two main classes: (1) $GABA_A$ receptors, which are members of the ligand-gated ion channel superfamily; and (2) $GABA_B$ receptors, which may be members of the G-protein linked receptor superfamily. Since the first cDNAs encoding individual $GABA_A$ receptor subunits were cloned the number of known members of the mammalian family has grown to include at least six $\alpha$ subunits, four $\beta$ subunits, three $\gamma$ subunits, one $\delta$ subunit, one $\epsilon$ subunit and two $\rho$ subunits.

Although knowledge of the diversity of the $GABA_A$ receptor gene family represents a huge step forward in our understanding of this ligand-gated ion channel, insight into the extent of subtype diversity is still at an early stage. It has been indicated that an $\alpha$ subunit, a $\beta$ subunit and a $\gamma$ subunit constitute the minimum requirement for forming a fully functional $GABA_A$ receptor expressed by transiently transfecting cDNAs into cells. As indicated above, $\delta$, $\epsilon$ and $\rho$ subunits also exist, but are present only to a minor extent in $GABA_A$ receptor populations.

Studies of receptor size and visualisation by electron microscopy conclude that, like other members of the ligand-gated ion channel family, the native $GABA_A$ receptor exists in pentameric form. The selection of at least one $\alpha$, one $\beta$ and one $\gamma$ subunit from a repertoire of seventeen allows for the possible existence of more than 10,000 pentameric subunit combinations. Moreover, this calculation overlooks the additional permutations that would be possible if the arrangement of subunits around the ion channel had no constraints (i.e. there could be 120 possible variants for a receptor composed of five different subunits).

Receptor subtype assemblies which do exist include, amongst many others, $\alpha 1\beta 2\gamma 2$, $\alpha 2\beta 2/3\gamma 2$, $\alpha 3\beta\gamma 2/3$, $\alpha 2\beta\gamma 1$, $\alpha 5\beta 3\gamma 2/3$, $\alpha 6\beta\gamma 2$, $\alpha 6\beta\delta$ and $\alpha 4\beta\delta$. Subtype assemblies containing an $\alpha 1$ subunit are present in most areas of the brain and are thought to account for over 40% of $GABA_A$ receptors in the rat. Subtype assemblies containing $\alpha 2$ and $\alpha 3$ subunits respectively are thought to account for about 25% and 17% of $GABA_A$ receptors in the rat. Subtype assemblies containing an $\alpha 5$ subunit are expressed predominantly in the hippocampus and cortex and are thought to represent about 4% of $GABA_A$ receptors in the rat.

A characteristic property of all known $GABA_A$ receptors is the presence of a number of modulatory sites, one of which is the benzodiazepine (BZ) binding site. The BZ binding site is the most explored of the $GABA_A$ receptor modulatory sites, and is the site through which anxiolytic drugs such as diazepam and temazepam exert their effect. Before the cloning of the $GABA_A$ receptor gene family, the benzodiazepine binding site was historically subdivided into two subtypes, BZ1 and BZ2, on the basis of radioligand binding studies. The BZ1 subtype has been shown to be pharmacologically equivalent to a $GABA_A$ receptor comprising the $\alpha 1$ subunit in combination with a $\beta$ subunit and $\gamma 2$. This is the most abundant $GABA_A$ receptor subtype, and is believed to represent almost half of all $GABA_A$ receptors in the brain.

Two other major populations are the $\alpha 2\beta\gamma 2$ and $\alpha 3\beta\gamma 2/3$ subtypes. Together these constitute approximately a further 35% of the total $GABA_A$ receptor repertoire. Pharmacologically this combination appears to be equivalent to the BZ2 subtype as defined previously by radioligand binding, although the BZ2 subtype may also include certain $\alpha 5$-containing subtype assemblies. The physiological role of these subtypes has hitherto been unclear because no sufficiently selective agonists or antagonists were known.

It is now believed that agents acting as BZ agonists at $\alpha 1\beta\gamma 2$, $\alpha 2\beta\gamma 2$ or $\alpha 3\beta\gamma 2$ subunits will possess desirable anxiolytic properties. Compounds which are modulators of the benzodiazepine binding site of the $GABA_A$ receptor by acting as BZ agonists are referred to hereinafter as "$GABA_A$ receptor agonists". The $\alpha 1$-selective $GABA_A$ receptor agonists alpidem and zolpidem are clinically prescribed as hypnotic agents, suggesting that at least some of the sedation associated with known anxiolytic drugs which act at the BZ1 binding site is mediated through $GABA_A$ receptors containing the $\alpha 1$ subunit. Accordingly, it is considered that $GABA_A$ receptor agonists which interact more favourably with the $\alpha 2$ and/or $\alpha 3$ subunit than with $\alpha 1$ will be effective in the treatment of anxiety with a reduced propensity to cause sedation. Also, agents which are antagonists or inverse agonists at $\alpha 1$ might be employed to reverse sedation or hypnosis caused by $\alpha 1$ agonists.

The compounds of the present invention, being selective ligands for $GABA_A$ receptors, are therefore of use in the treatment and/or prevention of a variety of disorders of the central nervous system. Such disorders include anxiety disorders, such as panic disorder with or without agoraphobia, agoraphobia without history of panic disorder, animal and other phobias including social phobias, obsessive-compulsive disorder, stress disorders including post-traumatic and acute stress disorder, and generalized or substance-induced anxiety disorder; neuroses; convulsions; migraine; depressive or bipolar disorders, for example single-episode or recurrent major depressive disorder, dysthymic disorder, bipolar I and bipolar II manic disorders, and cyclothymic disoder; psychotic disorders including schizophrenia; neurodegeneration arising from cerebral ischemia; attention deficit hyperactivity disorder; and disorders of circadian rhythm, e.g. in subjects suffering from the effects of jet lag or shift work.

Further disorders for which selective ligands for $GABA_A$ receptors may be of benefit include pain and nociception; emesis, including acute, delayed and anticipatory emesis, in particular emesis induced by chemotherapy or radiation, as well as post-operative nausea and vomiting; eating disorders including anorexia nervosa and bulimia nervosa; premenstrual syndrome; muscle spasm or spasticity, e.g. in paraplegic patients; and hearing loss. Selective ligands for $GABA_A$ receptors may also be effective as pre-medication prior to anaesthesia or minor procedures such as endoscopy, including gastric endoscopy.

In DE-A-2741763, and in U.S. Pat. Nos. 4,260,755, 4,260,756 and 4,654,343, are described various classes of 1,2,4-triazolo[4,3-b]pyridazine derivatives which are alleged to be useful as anxiolytic agents. The compounds described in DE-A-2741763 and in U.S. Pat. Nos. 4,260,755 and 4,654,343 possess a phenyl substituent at the 6-position of the triazolo-pyridazine ring system. The compounds described in U.S. Pat. No. 4,260,756, meanwhile, possess a heteroaryl moiety at the 6- or 8-position. In none of these publications, however, is there any disclosure or suggestion of 1,2,4-triazolo[4,3-b]pyridazine derivatives wherein the substituent at the 6-position is attached through a directly linked nitrogen atom.

EP-A-0085840 and EP-A-0134946 describe related series 1,2,4-triazolo[3,4-α]phthalazine derivatives which are stated to possess antianxiety activity. However, there is no disclosure nor any suggestion in either of these publications of replacing the benzo moiety of the triazolo-phthalazine ring system with any other functionality.

The present invention provides a class of triazolo-pyridazine derivatives which possess desirable binding properties at various $GABA_A$ receptor subtypes. The compounds in accordance with the present invention have good affinity as ligands for the α2 and/or α3 subunit of the human $GABA_A$ receptor. The compounds of this invention may interact more favourably with the α2 and/or α3 subunit than with the α1 subunit. Desirably, the compounds of the invention will exhibit functional selectivity in terms of a selective efficacy for the α2 and/or α3 subunit relative to the α1 subunit.

The compounds of the present invention are $GABA_A$ receptor subtype ligands having a binding affinity ($K_i$) for the α2 and/or α3 subunit, as measured in the assay described hereinbelow, of 100 nM or less, typically of 50 nM or less, and ideally of 10 nM or less. The compounds in accordance with this invention may possess at least a 2-fold, suitably at least a 5-fold, and advantageously at least a 10-fold, selective affinity for the α2 and/or α3 subunit relative to the α1 subunit. However, compounds which are not selective in terms of their binding affinity for the α2 and/or α3 subunit relative to the α1 subunit are also encompassed within the scope of the present invention; such compounds will desirably exhibit functional selectivity in terms of a selective efficacy for the α2 and/or α3 subunit relative to the α1 subunit.

The present invention provides a compound of formula I, or a salt or prodrug thereof:

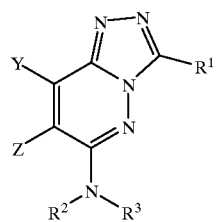

(I)

wherein

Y represents hydrogen or $C_{1-6}$ alkyl;

Z represents $C_{1-6}$ alkyl, $C_{3-7}$ cycloalkyl, $C_{4-7}$ cycloalkenyl, aryl, $C_{3-7}$ heterocycloalkyl, heteroaryl or di($C_{1-6}$)alkylamino, any of which groups may be optionally substituted;

$R^1$ represents $C_{3-7}$ cycloalkyl, phenyl, furyl, thienyl or pyridinyl, any of which groups may be optionally substituted;

$R^2$ represents hydrogen or $C_{1-6}$ alkyl; and $R^3$ represents hydrogen; or $C_{1-6}$ alkyl, $C_{3-7}$ cycloalkyl($C_{1-6}$)alkyl, propargyl, aryl($C_{1-6}$)alkyl, $C_{3-7}$ heterocycloalkyl($C_{1-6}$)alkyl or heteroaryl($C_{1-6}$)alkyl, any of which groups may be optionally substituted; or $R^2$ and $R^3$ are taken together with the intervening nitrogen atom to form a ring of formula (a) or (b):

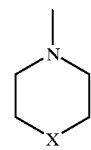

(a)

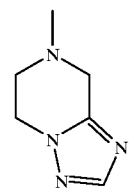

(b)

wherein

X represents oxygen, sulphur or N—$R^4$, in which $R^4$ represents hydrogen or $C_{1-6}$ alkyl.

The groups Z, $R^1$ and $R^3$ may be unsubstituted, or substituted by one or more, suitably by one or two, substituents. In general, the groups Z, $R^1$ and $R^3$ will be unsubstituted or monosubstituted. Examples of optional substituents on the groups Z, $R^1$ and $R^3$ include $C_{1-6}$ alkyl, aryl($C_{1-6}$)alkyl, pyridyl($C_{1-6}$)alkyl, halogen, halo($C_{1-6}$) alkyl, cyano, cyano($C_{1-6}$)alkyl, oxo, hydroxy, hydroxymethyl, $C_{1-6}$ alkoxy, $C_{3-7}$ cycloalkyl($C_{1-6}$)alkoxy, $C_{3-7}$ cycloalkoxy, amino, $C_{1-6}$ alkylamino, di($C_{1-6}$) alkylamino, amino($C_{1-6}$)alkyl, di($C_{1-6}$)alkylamino($C_{1-6}$) alkyl, di($C_{1-6}$)alkylaminocarbonyl($C_{1-6}$)alkyl, N-($C_{1-6}$) alkylpiperidinyl, pyrrolidinyl($C_{1-6}$)alkyl, piperazinyl($C_{1-6}$) alkyl, morpholinyl($C_{1-6}$)alkyl, di($C_{1-6}$)alkylmorpholinyl($C_{1-6}$)alkyl and imidazolyl($C_{1-6}$)alkyl. Representative substituents include $C_{1-6}$ alkyl, halogen, oxo, $C_{1-6}$ alkoxy and di($C_{1-6}$)alkylamino.

As used herein, the expression "$C_{1-6}$ alkyl" includes methyl and ethyl groups, and straight-chained or branched propyl, butyl, pentyl and hexyl groups. Particular alkyl groups are methyl, ethyl, n-propyl, isopropyl, tert-butyl and 1,1-dimethylpropyl. Derived expressions such as "$C_{1-6}$alkoxy" are to be construed accordingly.

Typical $C_{3-7}$ cycloalkyl groups include cyclopropyl, cyclobutyl, cyclopentyl and cyclohexyl.

The expression "$C_{3-7}$ cycloalkyl($C_{1-6}$)alkyl" as used herein includes cyclopropylmethyl, cyclobutylmethyl, cyclopentylmethyl and cyclohexylmethyl.

Typical $C_{4-7}$ cycloalkenyl groups include cyclobutenyl, cyclopentenyl and cyclohexenyl.

Typical aryl groups include phenyl and naphthyl, preferably phenyl.

The expression "aryl($C_{1-6}$)alkyl" as used herein includes benzyl, phenylethyl, phenylpropyl and naphthylmethyl.

Suitable heterocycloalkyl groups include azetidinyl, pyrrolidinyl, piperidinyl, piperazinyl, morpholinyl and thiomorpholinyl groups.

The expression "$C_{3-7}$ cycloalkyl($C_{1-6}$)alkyl" as used herein includes pyrrolidinylethyl, piperazinylethyl, morpholinylethyl, pyrrolidinylpropyl and morpholinylpropyl.

Suitable heteroaryl groups include pyridinyl, quinolinyl, isoquinolinyl, pyridazinyl, pyrimidinyl, pyrazinyl, quinoxalinyl, furyl, benzofuryl, dibenzofuryl, thienyl, benzthienyl, pyrrolyl, indolyl, pyrazolyl, indazolyl, oxazolyl, isoxazolyl, thiazolyl, isothiazolyl, imidazolyl, benzimidazolyl, oxadiazolyl, thiadiazolyl, triazolyl and tetrazolyl groups.

The expression "heteroaryl($C_{1-6}$)alkyl" as used herein includes furylmethyl, furylethyl, thienylmethyl, thienylethyl, pyrazolylmethyl, oxazolylmethyl, oxazolylethyl, isoxazolylmethyl, thiazolylmethyl, thiazolylethyl, imidazolylmethyl, imidazolylethyl, imidazolylpropyl, benzimidazolylmethyl, oxadiazolylmethyl, oxadiazolylethyl, thiadiazolylmethyl, thiadiazolylethyl, triazolylmethyl, triazolylethyl, tetrazolylmethyl, tetrazolylethyl, pyridinylmethyl, pyridinylethyl, pyridazinylmethyl, pyrimidinylmethyl, pyrazinylmethyl, quinolinylmethyl, isoquinolinylmethyl and quinoxalinylmethyl.

The term "halogen" as used herein includes fluorine, chlorine, bromine and iodine, especially fluorine or chlorine.

For use in medicine, the salts of the compounds of formula I will be pharmaceutically acceptable salts. Other salts may, however, be useful in the preparation of the compounds according to the invention or of their pharmaceutically acceptable salts. Suitable pharmaceutically acceptable salts of the compounds of this invention include acid addition salts which may, for example, be formed by mixing a solution of the compound according to the invention with a solution of a pharmaceutically acceptable acid such as hydrochloric acid, sulphuric acid, methanesulphonic acid, fumaric acid, maleic acid, succinic acid, acetic acid, benzoic acid, oxalic acid, citric acid, tartaric acid, carbonic acid or phosphoric acid. Furthermore, where the compounds of the invention carry an acidic moeity, suitable pharmaceutically acceptable salts thereof may include alkali metal salts, e.g. sodium or potassium salts; alkaline earth metal salts, e.g. calcium or magnesium salts; and salts formed with suitable organic ligands, e.g. quaternary ammonium salts.

The present invention includes within its scope prodrugs of the compounds of formula I above. In general, such prodrugs will be functional derivatives of the compounds of formula I which are readily convertible in vivo into the required compound of formula I. Conventional procedures for the selection and preparation of suitable prodrug derivatives are described, for example, in *Design of Prodrugs*, ed. H. Bundgaard, Elsevier, 1985.

Where the compounds according to the invention have at least one asymmetric centre, they may accordingly exist as enantiomers. Where the compounds according to the invention possess two or more asymmetric centres, they may additionally exist as diastereoisomers. It is to be understood that all such isomers and mixtures thereof in any proportion are encompassed within the scope of the present invention.

Suitably, Y represents hydrogen or methyl, especially hydrogen.

Examples of suitable values for the substituent Z include methyl, ethyl, isopropyl, tert-butyl, 1,1-dimethylpropyl, methyl-cyclopropyl, cyclobutyl, methyl-cyclobutyl, cyclopentyl, methyl-cyclopentyl, cyclohexyl, cyclobutenyl, phenyl, pyrrolidinyl, methyl-pyrrolidinyl, piperidinyl, morpholinyl, thiomorpholinyl, pyridinyl, furyl, thienyl, thienyl, chloro-thienyl and diethylamino.

In a particular embodiment, the substituent Z represents $C_{3-7}$ cycloalkyl, either unsubstituted or substituted $C_{1-6}$ alkyl, especially methyl. Favourably, Z represents cyclobutyl.

Examples of typical optional substituents on the group $R^1$ include methyl, fluoro and methoxy.

Representative values of $R^1$ include cyclopropyl, phenyl, methylphenyl, fluorophenyl, difluorophenyl, methoxyphenyl, furyl, thienyl, methyl-thienyl and pyridinyl. Suitably, $R^1$ may represent unsubstituted or monosubstituted phenyl. More particularly, $R^1$ represents phenyl.

Suitabley, $R^2$ represents hydrogen or methyl.

Suitable values for the substituent $R^3$ in the compounds according to the invention include hydrogen; and methyl, ethyl, propyl, butyl, cyclohexylmethyl, propargyl, benzyl, pyrrolidiniylethyl, piperazinylethyl, morpholinylethyl, pyrrolidinylpropyl, morpholinylpropyl, pyrazolylmethyl, isoxazolylmethyl, thiazolylmethyl, thiazolylethyl, imidazolylmethyl, imidazolylpropyl, benzimidazolylmethyl, oxadiazolylmethyl, triazolylmethyl, tetrazolylmethyl, pyridinylmethyl, pyridinylethyl, pyridazinylmethyl, pyrimidinylmethyl, pyrazinylmethyl, quinolinylmethyl, isoquinolinylmethyl and quinoaxalinylmethyl, any of which groups may be optionally substituted by one or more substituents. Typical values of $R^3$ include hydrogen; and methyl, ethyl, propyl, pyrrolidinylethyl, piperazinylethyl, morpholinylethyl, pyrrolidinylpropyl, morpholinylpropyl, imidazolylpropyl, triazolylmethyl, pyridinylmethyl and pyridinylethyl, any of which groups may be optionally substituted by one or more substituents.

Examples of suitable optional substituents on the group $R^3$ include $C_{1-6}$ alkyl, aryl($C_{1-6}$)alkyl, pyridyl($C_{1-6}$)alkyl, halogen, halo($C_{1-6}$)alkyl, cyano, cyano($C_{1-6}$)alkyl, oxo, hydroxymethyl, $C_{1-6}$alkoxy, $C_{3-7}$ cycloalkyl($C_{1-6}$)alkoxy, di($C_{1-6}$)alkylamino, amino($C_{1-6}$)alkyl, di($C_{1-6}$)alkylamino ($C_{1-6}$)alkyl, di($C_{1-6}$)alkylaminocarbonyl($C_{1-6}$)alkyl, N-($C_{1-6}$)alkylpiperidinyl, pyrrolidinyl($C_{1-6}$)alkyl, piperazinyl($C_{1-6}$)alkyl, morpholinyl($C_{1-6}$)alkyl and di($C_{1-6}$) alkylmorpholinyl($C_{1-6}$)alkyl, Typical substituents include $C_{1-6}$ alkyl, aryl($C_{1-6}$)alkyl, halogen, cyano, oxo hydroxymethyl, $C_{1-6}$ alkoxy, $C_{3-7}$ cycloalkyl($C_{1-6}$)alkoxy and di($C_{1-6}$)alkylamino, especially $C_{1-6}$ alkyl, oxo, $C_{1-6}$ alkoxy or di($C_{1-6}$)alkylamino.

Specific illustrations of particular substituents on the group $R^3$ include methyl, ethyl, n-propyl, benzyl, pyridinylmethyl, chloro, chloromethyl, cyano, cyanomethyl, oxo, hydroxymethyl, methoxy, ethoxy, cyclopropylmethoxy, dimethylamino, dimethylaminomethyl, aminoethyl, dimethylaminoethyl, dimethylaminocarbonylmethyl, N-methylpiperidinyl, pyrrolidinylethyl, piperazinylethyl, morpholinylmethyl and dimethylmorpholinylmethyl, especially methyl, oxo, methoxy or dimethylamino.

Representative values of $R^3$ include hydrogen, methyl, cyanomethyl, methoxyethyl, dimethylaminoethyl, dimethylaminopropyl, hydroxybutyl, hydroxymethyl-cyclohexylmethyl, propargyl, dimethylaminomethyl-propargyl, dimethylmorphinolinylmethyl-propargyl, cyanobenzyl, hydroxymethyl-benzyl, methyl-pyrrolidinylethyl, piperazinylethyl, morpholinylethyl, pyrrolidinylpropyl, pyrrolidinonylpropyl, morpholinylpropyl, pyrazolylmethyl, dimethyl-pyrazolylmethyl, methyl-isoxazolylmethyl, thiazolylmethyl, methyl-thiazolylmethyl, ethyl-thiazolylmethyl, methyl-thiazolylethyl, imidazolylmethyl, methyl-imidazolylmethyl, ethyl-imidazolylmethyl, benzyl-imidazolylmethyl, imidazolylpropyl, benzimadozolylmethyl, methyl-oxadiazolylmethyl, triazolylmethyl, methyl-triazolylmethyl, propyl-triazolylmethyl, benzyl-triazolylmethyl, pyridinylmethyl-triazolylmethyl, cyanomethyl-triazolylmethyl, dimethylaminomethyl-triazolylmethyl, aminoethyl-triazolylmethyl, dimethylaminoethyl-triazolylmethyl, dimethylaminocarbonylmethyl-triazolylmethyl, N-methylpiperidinyl-triazolylmethyl, pyrrolidinylethyl-triazolylmethyl, piperazinylethyl-triazolylmethyl, morpholinylethyl-triazolylmethyl, methyl-tetrazolylmethyl, pyridinylmethyl, methyl-pyridinylmethyl, dimethyl-pyridinylmethyl, ethoxy-pyridinylmethyl, cyclopropylmethoxy-pyridinylmethyl, pyridinylethyl, pyridazinylmethyl, chloro-pyridazinylmethyl, pyrimidinylmethyl, pyrazinylmethyl, quinolinylmethyl, isoquinolinylmethyl and quinoxalinylmethyl.

Particular values of $R^3$ include hydrogen, methyl, methoxyethyl, dimethylaminoethyl, dimethylaminopropyl, methyl-pyrrolidinylethyl, piperazinylethyl, morpholinylethyl, pyrrolidinylpropyl, pyrrolidinonylpropyl, morpholinylpropyl, imidazolylpropyl, methyl-triazolylmethyl, pyridinylmethyl and pyridinylethyl.

A favoured value of $R^3$ is methyl-triazolylmethyl.

Suitably, $R^4$ represents hydrogen or methyl.

Where $R^2$ and $R^3$ are taken together with the intervening nitrogen atom to form a ring of formula (a) as depicted above, the moiety X suitably represents oxygen.

A particular sub-class of compounds according to the invention is represented by the compounds of formula IIA, and salts and prodrugs thereof:

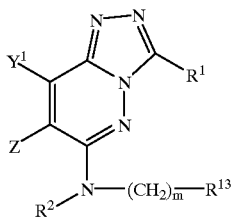

(IIA)

wherein
$Y^1$ represents hydrogen or methyl;
Z, $R^1$ and $R^2$ are as defined with reference to formula I above;
M is 1, 2 or 3, preferably 1; and
$R^{13}$ represents aryl or heteroaryl, either of which groups may be optionally substituted by one or more substituents.

Suitably, $Y^1$ represents hydrogen.

Examples of typical substituents on the group $R^{13}$ include $C_{1-6}$ alkyl, aryl($C_{1-6}$)alkyl, pyridyl($C_{1-6}$)alkyl, halogen, cyano, cyano($C_{1-6}$)alkyl, hydroxymethyl, $C_{1-6}$ alkoxy, $C_{3-7}$ cycloalkyl($C_{1-6}$)alkoxy, di($C_{1-6}$)alkylamino($C_{1-6}$)alkyl, amino($C_{1-6}$)alkyl, di($C_{1-6}$)alkylaminocarbonyl($C_{1-6}$)alkyl, N-($C_{1-6}$)alkylpiperdinyl, pyrrolidinyl($C_{1-6}$)alkyl, piperazinyl($C_{1-6}$)alkyl and morpholinyl($C_{1-6}$)alkyl, especially $C_{1-6}$ alkyl or $C_{1-6}$ alkoxy.

Illustrative values of specific substituents on the group $R^{13}$ include methyl, ethyl, n-propyl, benzyl, pyridinylmethyl, chloro, cyano, cyanomethyl, hydroxymethyl, methoxy, ethoxy, cyclopropylmethoxy, dimethylaminomethyl, aminoethyl, dimethylaminoethyl, dimethylaminocarbonylmethyl, N-methylpiperidinyl, pyrrolidinylethyl, piperazinylethyl and morpholinylmethyl, especially methyl.

Particular values of $R^{13}$ include cyanophenyl, hydroxymethyl-phenyl, pyrazolyl, dimethyl-pyrazolyl, methyl-isoxazolyl, thiazolyl, methyl-thiazolyl, ethyl-thiazolyl, imidazolyl, methyl-imidazolyl, ethyl-imidazolyl, benzyl-imidazolyl, benzimidazolyl, methyl-oxadiazolyl, triazolyl, methyl-triazolyl, propyl-triazolyl, benzyl-triazolyl, pyridinylmethyl-triazolyl, cyanomethyl-triazolyl, dimethylaminomethyl-triazolyl, aminoethyl-triazolyl, dimethylaminoethyl-triazolyl, dimethylaminocarbonylmethyl-triazolyl, N-methylpiperidinyl-triazolyl, pyrrolidinylethyl-triazolyl, piperazinylethyl-triazolyl, morpholinylethyl-triazolyl, methyl-tetrazolyl, pyridinyl, methyl-pyridinyl, dimethyl-pyridinyl, ethoxy-pyridinyl, cyclopropylmethoxy-pyridinyl, pyridazinyl, chloro-pyrdiazinyl, pyrimidinyl, pyrazinyl, quinolinyl, isoquinolinyl and quinoxoaliny.

Specific values of $R^{13}$ include imidazolyl, methyl-triazolyl and pyridinyl.

A favoured value of $R^{13}$ is methyl-triazolyl.

A particular subset of the compounds of formula IIA above is represented by the compounds of formula IIB, and pharmaceutically acceptable salts thereof:

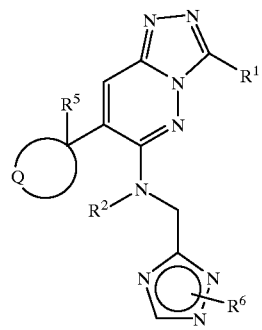

(IIB)

wherein
$R^1$ and $R^2$ are as defined with reference to formula I above;
Q represents the residue of a cyclopropyl, cyclobutyl, cyclopentyl or cyclohexyl ring;
$R^5$ represents hydrogen or methyl; and
$R^6$ represents hydrogen or methyl.

In relation to formula IIB above, $R^1$ suitable represents phenyl.

In a favoured embodiment, Q suitably represents the residue of a cyclobutyl ring.

Suitably, $R^5$ represents hydrogen.

Suitably, $R^6$ represents methyl.

Specific compounds within the scope of the present invention include:

N-(7-cyclobutyl-3-phenyl-1,2,4-triazolo[4,3-b]pyridazin-6-yl)-N-(1-methyl-1H-1,2,4-triazol-3-ylmethyl)amine;

N-(7-cyclobutyl-3-phenyl-1,2,4-triazolo[4,3-b]pyridazin-6-yl)-N,N-dimethylamine;

N-(7-cyclobutyl-3-phenyl-1,2,4-triazolo[4,3-b]pyridazin-6-yl)-N-methyl-N-(1-methyl-1H-1,2,4-triazol-3-ylmethyl)amine;

7-cyclobutyl-6-(5,6-dihydro-8H-1,2,4-triazolo[1,5-α]pyrazin-7-yl)-3-phenyl-1,2,4-triazolo[4,3-b]pyridazine;

7-cyclobutyl-3-phenyl-1,2,4-triazolo[4,3-b]pyridazin-6-ylamine;

N-(7-cyclobutyl-3-phenyl-1,2,4-triazolo[4,3-b]pyridazin-6-yl)-N-methylamine;

7-cyclobutyl-6-(morpholin-4-yl)-3-phenyl-1,2,4-triazolo[4,3-b]pyridazine;

N-(7-cyclobutyl-3-phenyl-1,2,4-triazolo[4,3-b]pyridazin-6-yl)-N-(2-methoxyethyl)amine;

N-(7-cyclobutyl-3-phenyl-1,2,4-triazolo[4,3-b]pyridazin-6-yl)-N-(pyridin-2-ylmethyl)amine;

N'-(7-cyclobutyl-3-phenyl-1,2,4-triazolo[4,3-b]pyridazin-6-yl)-N,N-dimethylethane-1,2-diamine;

N-(7-cyclobutyl-3-phenyl-1,2,4-triazolo[4,3-b]pyridazin-6-yl)-N-[3-(morpholin-4-yl)propyl]amine;

(±)-N-(7-cyclobutyl-3-phenyl-1,2,4-triazolo[4,3-b]pyridazin-6-yl)-N-[2-(1-methylpyrrolidin-2-yl)ethyl]amine;

N'-(7-cyclobutyl-3-phenyl-1,2,4-triazolo[4,3-b]pyridazin-6-yl)-N,N-dimethylpropane-1,3-diamine;
N-(7-cyclobutyl-3-phenyl-1,2,4-triazolo[4,3-b]pyridazin-6-yl)-N-[3-(imidazol-1-yl)propyl]amine;
N-(7-cyclobutyl-3-phenyl-1,2,4-triazolo[4,3-b]pyridazin-6-yl)-N-[3-(pyrrolidin-1-yl)propyl]amine;
1-[3-(7-cyclobutyl-3-phenyl-1,2,4-triazolo[4,3-b]pyridazin-6-ylamino)-propyl]pyrrolidin-2-one;
N-(7-cyclobutyl-3-phenyl-1,2,4-triazolo[4,3-b]pyridazin-6-yl)-N-[2-(piperazin-1-yl)ethyl]amine;
N-(7-cyclobutyl-3-phenyl-1,2,4-triazolo[4,3-b]pyridazin-6-yl)-N-[2-(morpholin-4-yl)ethyl]amine;
N-(7-cyclobutyl-3-phenyl-1,2,4-triazolo[4,3-b]pyridazin-6-yl)-N-[2-(pyridin-2-yl)ethyl]amine;
and salts and prodrugs thereof.

Also provided by the present invention is a method for the treatment and/or prevention of anxiety which comprises administering to a patient in need of such treatment an effective amount of a compound of formula I as defined above or a pharmaceutically acceptable salt thereof or a prodrug thereof.

Further provided by the present invention is a method for the treatment and/or prevention of convulsions (e.g. in a patient suffering from epilepsy or a related disorder) which comprises administering to a patient in need of such treatment an effective amount of a compound of formula I as defined above or a pharmaceutically acceptable salt thereof or a prodrug thereof.

The binding affinity ($K_i$) of the compounds according to the present invention for the $\alpha 3$ subunit of the human $GABA_A$ receptor is conveniently as measured in the assay described hereinbelow. The $\alpha 3$ subunit binding affinity ($K_i$) of the compounds according to the invention is ideally 10 nM or less, preferably 2 nM or less, and more preferably 1 nM or less.

The compounds according to the present invention will ideally elicit at least a 40%, preferably at least a 50%, and more preferably at least a 60%, potentiation of the GABA $EC_{20}$ response in stably transfected recombinant cell lines expressing the $\alpha 3$ subunit of the human $GABA_A$ receptor. Moreover, the compounds of the invention will ideally elicit at most a 30%, preferably at most a 20%, and more preferably at most a 10%, potentiation of the GABA $EC_{20}$ response in stably transfected recombinant cell lines expressing the $\alpha 1$ subunit of the human $GABA_A$ receptor.

The potentiation of the GABA $EC_{20}$ response in stably transfected cell lines expressing the $\alpha 3$ and $\alpha 1$ subunits of the human $GABA_A$ receptor can conveniently be measured by procedures analogous to the protocol described in Wafford et al., *Mol. Pharmacol.*, 1996, 50, 670–678. The procedure will suitably be carried out utilising cultures of stably transfected eukaryotic cells, typically of stably transfected mouse Ltk fibroblast cells.

The compounds according to the present invention exhibit anxiolytic activity, as may be demonstrated by a positive response in the elevated plus maze and conditioned suppression of drinking tests (cf. Dawson et al., *Psychopharmacology*, 1995, 121, 109–117). Moreover, the compounds of the invention are substantially non-sedating, as may be confirmed by an appropriate result obtained from the response sensitivity (chain-pulling) test (cf. Bayley et al., *J. Psychopharmacol.*, 1996, 10, 206–213).

The compounds according to the present invention may also exhibit anticonvulsant activity. This can be demonstrated by the ability to block pentylenetetrazole-induced seizures in rats and mice, following a protocol analogous to that described by Bristow et al. in *J. Pharmacol. Exp. Ther.*, 1996, 279, 492–501.

In order to elicit their behavioural effects, the compounds of the invention will be brain-penetrant; in other words, these compounds will be capable of crossing the so-called "blood-brain barrier". Preferably, the compounds of the invention will be capable of exerting their beneficial therapeutic action following administration by the oral route.

The invention also provides pharmaceutical compositions comprising one or more compounds of the invention in association with a pharmaceutically acceptable carrier. Preferably these compositions are in unit dosage forms such as tablets, pills, capsules, powders, granules, sterile parenteral solutions or suspensions, metered aerosol or liquid sprays, drops, ampoules, auto-injector devices or suppositories; for oral, parenteral, intranasal, sublingual or rectal administration, or for administration by inhalation or insufflation. For preparing solid compositions such as tablets, the principal active ingredient is mixed with a pharmaceutical carrier, e.g. conventional tableting ingredients such as corn starch, lactose, sucrose, sorbitol, talc, stearic acid, magnesium stearate, dicalcium phosphate or gums, and other pharmaceutical diluents, e.g. water, to form a solid preformulation composition containing a homogeneous mixture of a compound of the present invention, or a pharmaceutically acceptable salt thereof. When referring to these preformulation compositions as homogeneous, it is meant that the active ingredient is dispersed evenly throughout the composition so that the composition may be readily subdivided into equally effective unit dosage forms such as tablets, pills and capsules. This solid preformulation composition is then subdivided into unit dosage forms of the type described above containing from 0.1 to about 500 mg of the active ingredient of the present invention. Typical unit dosage forms contain from 1 to 100 mg, for example, 1, 2, 5, 10, 25, 50 or 100 mg, of the active ingredient. The tablets or pills of the novel composition can be coated or otherwise compounded to provide a dosage form affording the advantage of prolonged action. For dosage component, the latter being in the form of an envelope over the former. The two components can be separated by an enteric layer which serves to resist disintegration in the stomach and permits the inner component to pass intact into the duodenum or to be delayed in release. A variety of materials can be used for such enteric layers or coatings, such materials including a number of polymeric acids and mixtures of polymeric acids with such materials as shellac, cetyl alcohol and cellulose acetate.

The liquid forms in which the novel compositions of the present invention may be incorporated for administration orally or by injection include aqueous solutions, suitably flavoured syrups, aqueous or oil suspensions, and flavoured emulsions with edible oils such as cottonseed oil, sesame oil, coconut oil or peanut oil, as well as elixirs and similar pharmaceutical vehicles. Suitable dispersing or suspending agents for aqueous suspensions include synthetic and natural gums such as tragacanth, acacia, alginate, dextran, sodium carboxymethylcellulose, methylcellulose, polyvinylpyrrolidone or gelatin.

In the treatment of anxiety, a suitable dosage level is about 0.01 to 250 mg/kg per day, preferably about 0.05 to 100 mg/kg per day, and especially about 0.05 to 5 mg/kg per day. The compounds may be administered on a regimen of 1 to 4 times per day.

The compounds of formula I as defined above may be prepared by a process which comprises reacting a compound of formula III with a compound of formula IV:

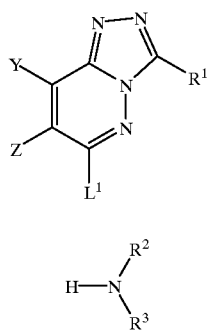

(III)

(IV)

wherein Y, Z, $R^1$, $R^2$ and $R^3$ are as defined above; and $L^1$ represents a suitable leaving group.

The leaving group $L^1$ is typically a halogen atom, especially chloro.

The reaction between compounds III and IV is conveniently effected by heating the reactants together in a sealed tube, optionally in a suitable solvent such as N,N-dimethylformamide, methanol or 1,4-dioxane, and optionally in the presence of a base such as triethylamine. Where $R^2$ and $R^3$ together with the intervening nitrogen atom represent a ring of formula (b) as defined above, the reaction between compounds III and IV may conveniently be effected by stirring the reactants in an inert solvent, e.g. dimethyl sulphoxide, at an elevated temperature, typically in the region of 150° C.

The intermediates of formula III above may be prepared by reacting a compound of formula V with a substantially equimolar amount of a hydrazine derivative of formula VI:

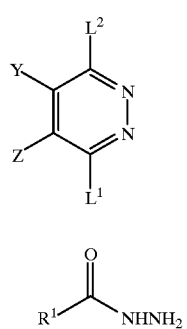

(V)

(VI)

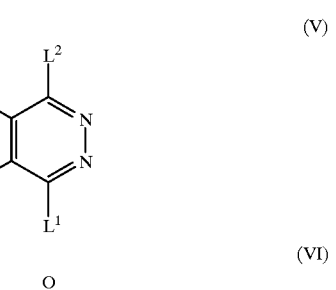

wherein Y, Z, $R^1$ and $L^1$ are as defined above, and $L^2$ represents a suitable leaving group; followed, if necessary, by separation of the resulting mixture of isomers by conventional means.

The leaving group $L^2$ is typically a halogen atom, especially chloro. In the intermediates of formula V, the leaving groups $L^1$ and $L^2$ may be the same or different, but are suitably the same, preferably both chloro.

The reaction between compounds V and VI is conveniently effected by heating the reactants in the presence of a proton source such as triethylamine hydrochloride, typically at reflux in an inert solvent such as xylene or 1,4-dioxane.

Where Y and Z are different, the reaction between compounds V and VI will, as indicated above, usually give rise to a mixture of isomeric products depending upon whether the hydrazine derivative VI displaces the leaving group $L^1$ or $L^2$. Thus, in addition to the required product of formula III, the isomeric compound wherein the Y and Z moieties are reversed will usually be obtained to some extent. For this reason it will generally be necessary to separate the resulting mixture of isomers by conventional methods such as chromatography.

In another procedure, the compounds of formula I as defined above may be prepared by a process which comprises reacting a compound of formula Z—$CO_2$H with a compound of formula VII:

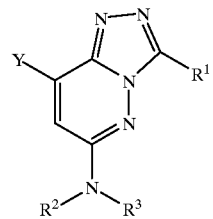

(VII)

wherein Y, Z, $R^1$, $R^2$ and $R^3$ are as defined above; in the presence of silver nitrate and ammonium persulphate.

The reaction is conveniently carried out under acidic conditions in a suitable solvent, for example using sulphuric acid in water or aqueous acetonitrile, typically at an elevated temperature.

The intermediates of formula VII correspond to the compounds of formula I as defined above wherein Z is hydrogen, and they may therefore be prepared by methods analogous to those described above for preparing the corresponding compounds of formula I.

In a further procedure, the compounds of formula I as defined above may be prepared by a process which comprises reacting a compound of formula VIII with a compound of formula IX:

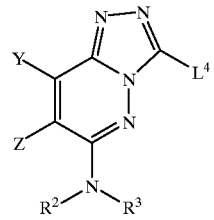

(VIII)

(IX)

$R^1$—M wherein Y, Z, $R^1$, $R^2$ and $R^3$ are as defined above, M represents —$B(OH)_2$ or —$Sn(Alk)_3$ in which Alk represents a $C_{1-6}$ alkyl group, typically n-butyl, and $L^4$ represents a suitable leaving group; in the presence of a transition metal catalyst.

The leaving group $L^4$ is suitably a halogen atom, e.g. bromo.

A suitable transition metal catalyst of use in the reaction between compounds VIII and IX comprises dichlorobis (triphenylphosphine)-palladium(II) or tetrakis (triphenylphosphine)palladium(0).

The reaction between compounds VIII and IX is conveniently effected in an inert solvent such as N,N-dimethylformamide, typically at an elevated temperature.

The intermediates of formula VIII may be prepared by reacting a compound of formula IV as defined above with a compound of formula X:

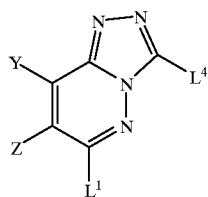

(X)

wherein Y, Z, $L^1$ and $L^4$ are as defined above; under conditions analogous to those described above for the reaction between compounds III and IV.

The intermediates of formula V above may be prepared by reacting a compound of formula Z—$CO_2$H with a compound of formula XI:

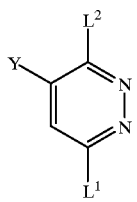

(XI)

wherein Y, Z, $L^1$ and $L^2$ are as defined above; in the presence of silver nitrate and ammonium persulphate; under conditions analogous to those described above for the reaction between Z—$CO_2$H and compound VII.

Where they are not commercially available, the starting materials of formula IV, VI, IX, X, and XI may be prepared by methods analogous to those described in the accompanying Examples, or by standard methods well known from the art.

It will be understood that any compound of formula I initially obtained from any of the above processes may, where appropriate, subsequently be elaborated into a further compound of formula I by techniques known from the art. For example, a compound of formula I initially obtained wherein $R^3$ is unsubstituted may be converted into a corresponding compound wherein $R^3$ is substituted, typically be standard alkylation procedures, for example by treatment with a haloalkyl derivative in the presence of sodium hydride and N,N-dimethylformamide, or with a hydroxyalkyl derivative in the presence of triphenylphosphine and diethyl azodicarboxylate. Furthermore, a compound of formula I initially obtained wherein $R^3$ represents cyano($C_{1-6}$) alkyl may be converted into the corresponding 3-substituted 1,2,4-triazol-5-yl($C_{1-6}$)alkyl analogue by treatment with the appropriate acyl hydrazine derivative in the presence of a base such as sodium methoxide. Similarly, a compound of formula I initially obtained wherein $R^3$ represents an optionally substituted propargyl moiety may be converted into the corresponding 1,2,3-triazolylmethyl analogue by treatment with azide anion. A compound of formula I initially obtained wherein the $R^3$ substituent is substituted by a halogen atom, e.g. chloro, may be converted into the corresponding compound wherein the $R^3$ substituent is substituted by a di($C_{1-6}$)alkylamino moiety by treatment with the appropriate di($C_{1-6}$)alkylamine, typically with heating in a solvent such as 1,4-dioxane in a sealed tube.

Where the above-described processes for the preparation of the compounds according to the invention give rise to mixtures of stereoisomers, these isomers may be separated by conventional techniques such as preparative chromatography. The novel compounds may be prepared in racemic form, or individual enantiomers may be prepared either by enantiospecific synthesis or by resolution. The novel compounds may, for example, be resolved into their component enantiomers by standard techniques such as preparative HPLC, or the formation of diastereomeric pairs by salt formation with an optically active acid, such as (−)-di-p-toluoyl-d-tartaric acid and/or (+)-di-p-toluoyl-l-tartaric acid, followed by fractional crystallization and regeneration of the free base. The novel compounds may also be resolved by formation of diastereomeric esters or amides, followed by chromatographic separation and removal of the chiral auxiliary.

During any of the above synthetic sequences it may be necessary and/or desirable to protect sensitive or reactive groups on any of the molecules concerned. This may be achieved by means of conventional protecting groups, such as those described in *Protective Groups in Organic Chemistry*, ed. J. F. W. McOmie, Plenum Press, 1973; and T. W. Greene & P. G. M. Wuts, *Protective Groups in Organic Synthesis*, John Wiley & Sons, 1991. The protecting groups may be removed at a convenient subsequent stage using methods known from the art.

The following Examples illustrate the preparation of compounds according to the invention.

The compounds in accordance with this invention potently inhibit the binding of [$^3$H]-flumazenil to the benzodiazepine binding site of human $GABA_A$ receptors containing the α2 or α3 subunit stably expressed in Ltk cells.

Reagents

Phosphate buffered saline (PBS).

Assay buffer: 10 mM $KH_2PO_4$, 100 mM KCl, pH 7.4 at room temperature.

[$^3$H]-Flumazenil (18 nM for α1β3γ2 cells; 18 nM for α2β3γ2 cells; 10 nM for α3β3γ2 cells) in assay buffer.

Flunitrazepam 100 μM in assay buffer.

Cells resuspended in assay buffer (1 tray to 10 ml).

Haversting Cells

Supernatant is removed from cells. PBS (approximately 20 ml) is added. The cells are scraped and placed in a 50 ml centrifuge tube. The procedure is repeated with a further 10 ml of PBS to ensure that most of the cells are removed. The cells are pelleted by centrifuging for 20 min at 3000 rpm in a benchtop centrifuge, and then frozen if desired. The pellets are resuspended in 10 ml of buffer per tray (25 cm×25 cm) of cells.

Assay

Can be carried out in deep 96-well plates or in tubes. Each tube contains:

300 μl of assay buffer.

50 μl of [$^3$H]-flumazenil (final concentration for α1β3γ2: 1.8 nM; for α2β3γ2: 1.8 nM; for α3β3γ2: 1.0 nM).

50 μl of buffer or solvent carrier (e.g. 10% DMSO) if compounds are dissolved in 10% DMSO (total); test compound or flunitrazepam (to determine non-specific binding), 10 μM final concentration.

100 μl of cells.

Assays are incubated for 1 hour at 40° C., then filtered using either a Tomtec or Brandel cell harvester onto GF/B filters followed by 3×3 ml washes with ice cold assay buffer. Filters are dried and counted by liquid scintillation counting. Expected values for total binding are 3000–4000 dpm for total counts and less than 200 dpm for non-specific binding if using liquid scintillation counting, or 1500–2000 dpm for total counts and less than 200 dpm for non-specific binding if counting with meltilex solid scintillant. Binding parameters are determined by non-linear least squares regression analysis, from which the inhibition constant $K_i$ can be calculated for each test compound.

The compounds of the accompanying Examples were tested in the above assay, and all were found to possess a $K_i$ value for displacement of [$^3$H]-flumazenil from the α2 and/or α3 subunit of the human $GABA_A$ receptor of 100 nM or less.

EXAMPLE 1

N-(7-Cyclobutyl-3-phenyl-1,2,4-triazolo[4,3-b] pyridazin-6-yl)-N-(1-methyl-1H-1,2,4-triazol-3-ylmethyl)amine and N-(7-Cyclobutyl-3-phenyl-1,2,4-triazolo[4,3-b] pyridazin-6-yl)-N,N-dimethylamine a) 3,6-Dichloro-4-cyclobutylpyridazine Concentrated sulphuric acid (53.6 ml, 1.0 mol) was added carefully to a stirred suspension of 3,6-dichloropyridazine (50.0 g, 0.34 mol) in water (1.25 l). This mixture was then heated to 70° C. (internal temperature) before the addition of cyclobutane carboxylic acid (35.3 ml, 0.37 mol). A solution of silver nitrate (11.4 g, 0.07 mol) in water (20 ml) was then added over approximately one minute. This caused the reaction mixture to become milky in appearance. A solution of ammonium persulphate (230 g, 1.0 mol) in water (0.63 l) was then added over 20–30 minutes. The internal temperature rose to approximately 85° C. During the addition the product formed as a sticky precipitate. Upon complete addition the reaction was stirred for an additional 5 minutes, then allowed to cool to room temperature. The mixture was then poured onto ice and basified with concentrated aqueous ammonia, with the addition of more ice as required to keep the temperature below 10° C. The aqueous phase was extracted with dichloromethane (x3). The combined extracts were dried ($MgSO_4$), filtered and evaporated to give the title compound (55.7 g, 82%) as an oil. $^1$H nmr ($CDCl_3$) indicated contamination with approximately 5% of the 4,5-dicyclobutyl compound. However, this material was used without further purification. Data for the title compound: $^1$H NMR (360 MHz, $d_6$-DMSO) δ 1.79–1.90 (1H, m), 2.00–2.09 (1H, m), 2.18–2.30 (2H, m), 2.33–2.40 (2H, m), 3.63–3.72 (1H, m), 7.95 (1H, s); MS ($ES^+$) m/e 203 [MH]$^+$, 205 [MH]$^+$, 207 [MH]$^+$.

b) 6-Chloro-7-cyclobutyl-3-phenyl-1,2,4-triazolo[4,3-b] pyridazine

A mixture of 3,6-dichloro-4-cyclobutylpyridazine from above (55.7 g, 0.27 mol), benzoic hydrazide (41.1 g, 0.30 mol) and triethylamine hydrochloride (41.5 g, 0.30 mol) in p-xylene (0.4 l) was stirred and heated at reflux under a stream of nitrogen for 24 hours. Upon cooling the volatiles were removed in vacuo. The residue was partitioned between dichloromethane and water. The aqueous was basified by the addition of solid potassium carbonate. Some dark insoluble material was removed by filtration at this stage. The aqueous phase was further extracted with dichloromethane (x2). The combined extracts were dried ($MgSO_4$), filtered and evaporated. The residue was purified by chromatography on silica gel eluting with 5%→10%→25% ethyl acetate/dichloromethane to give the title compound, (26.4 g, 34%) as an off-white solid. Data for the title compound: $^1$H NMR (360 MHz, $CDCl_3$) δ 1.90–2.00 (1H, m), 2.12–2.28 (3H, m), 2.48–2.57 (2H, m), 3.69–3.78 (1H, m), 7.49–7.59 (3H, m), 7.97 (1H, s), 8.45–8.48 (2H, m); MS ($ES^+$) m/e 285 [MH]$^+$, 287 [MH]$^+$.

c) 3-Chloromethyl-1-methyl-1H-1,2,4-triazole (1-Methyl-1H-1,2,4-triazol-3-yl)methanol (500 mg, 4.4 mmol) (prepared using the conditions described in EP-A-421210) was added portionwise to thionyl chloride (5 ml) at 0° C. Upon complete addition the mixture was allowed to warm to room temperature, then heated at reflux for 45 minutes (gas evolution observed). Upon cooling the thionyl chloride was removed in vacuo. The residue was partitioned between dichloromethane and aqueous sodium hydrogen carbonate. The aqueous phase was further extracted with dichloromethane (x2). The combined extracts were dried ($Na_2SO_4$), filtered and evaporated to give the title chloride (570 mg), as an oil. This material was used without further purification. Data for the title compound: $^1$H NMR (250 MHz, $CDCl^3$) δ 3.92 (3H, s), 4.63 (2H, s), 8.10 (1H, s). MS ($ES^+$) m/e 133 [MH]$^+$, 131 [MH]$^+$.

d) C-(1-Methyl-1H-1,2,4-triazol-3-yl)methylamine Hydrochloride

A solution of 3-chloromethyl-1-methyl-1H-1,2,4-triazole (600 mg, 4.6 mmol) in aqueous ammonia (5 ml) was stirred and heated at 80° C. for 16 hours in a sealed tube. Upon cooling the volatiles were removed in vacuo (azeotroping with ethanol) to give the title compound (600 mg, 92%) as a colourless solid after drying under high vacuum. $^1$H NMR (250 MHz, $d_6$-DMSO) δ 3.88 (3H, s), 4.04 (2H, s), 8.3 (3H, br s), 8.58 (1H, s).

e) N-(7-Cyclobutyl-3-phenyl-1,2,4-triazolo[4,3-b] pyridazin-6-yl)-N-(1-methyl-1H-1,2,4-triazol-3-ylmethyl) amine and N-(7-Cyclobutyl-3-phenyl-1,2,4-triazolo[4,3-b] pyridazin-6-yl)-N,N-dimethylamine A mixture of 6-chloro-7-cyclobutyl-3-phenyl-1,2,4-triazolo[4,3-b]pyridazine (144 mg, 0.52 mmol) and C-(1-methyl-1H-1,2,4-triazol-3-yl)methylamine hydrochloride (300 mg, 2.0 mmol) in triethylamine (1 ml) and dry DMF (1 ml) was stirred and heated at 100° C. in a sealed tube for 20 hours. Upon cooling the volatiles were removed in vacuo, and the residue was partitioned between dichloromethane and saturated aqueous sodium hydrogen carbonate. The aqueous was further extracted with dichloromethane (x2). The combined extracts were dried ($Na_2SO_4$), filtered and evaporated. The residue was purified by chromatograhy on silica gel, eluting with 2%→5%→10% methanol-dichloromethane to give, in order of elution:

N-(7-cyclobutyl-3-phenyl-1,2,4-triazolo[4,3-b]pyridazin-6-yl)-N,N-dimethylamine: $^1$H NMR (360 MHz, $CDCl_3$) δ 1.90–2.23 (4H, m), 2.44–2.52 (2H, m), 2.94 (6H, s), 3.66–3.74 (1H, m), 7.44–7.55 (3H, m), 7.90 (1H, s), 8.55 (2H, d, J=8 Hz); MS ($ES^+$) m/e 294 [MH]$^+$; and N-(7-cyclobutyl-3-phenyl-1,2,4-triazolo[4, 3-b]pyridazin-6-yl)-N-(1-methyl-1H-1,2,4-triazol-3-ylmethyl)amine: $^1$H NMR (360 MHz, $CDCl_3$) δ 1.96–2.02 (1H, m), 2.18–2.32 (3H, m), 2.50–2.56 (2H, m), 3.48–3.54 (1H, m), 3.94 (3H, s), 4.73 (2H, d, J=4.6 Hz), 5.45 (1H, br s), 7.44–7.56 (3H, m), 7.69 (1H, d, J=1.5 Hz), 8.02 (1H, s), 8.58 (2H, d, J=8 Hz); MS ($ES^+$) m/e 3.61 [MH]$^+$.

EXAMPLE 2

N-(7-Cyclobutyl-3-phenyl-1,2,4-triazolo[4,3-b] pyridazin-6-yl)-N-methyl-N-(1-methyl-1H-1,2,4-triazol-3- ylmethyl)amine Hydrochloride a) N-Methyl-N-(1-methyl-1H-1,2,4-triazol-3-ylmethyl) amine A solution of 3-chloromethyl-1-methyl-1H-1,2,4-triazole (from Example 1, Step c; 600 mg, 4.6 mmol) in 40% aqueous methylamine and 1,4-dioxane (5 ml) was stirred and heated at 80° C. in a sealed tube for 16 hours. Upon cooling the whole mixture was evaporated (azeotroping with ethanol). The residue was purified by chromatography on silica gel, eluting with dichloromethane-methanol-aqueous ammonia (60:8:1→40:8:1) to give the title compound (440 mg, 80%) as a pale yellow oil. $^1$H NMR (250 MHz, d$_6$-DMSO) δ 3.61 (2H, s), 3.81 (3H, s), 8.35 (1H, s); MS (ES$^+$) m/e 127 [MH]$^+$.

b) N-(7-Cyclobutyl-3-phenyl-1,2,4-triazolo[4,3-b]pyridazin-6-yl)-N-methyl-N-(1-methyl-1H-1,2,4-triazol-3-ylmethyl)amine Hydrochloride A mixture of 6-chloro-7-cyclobutyl-3-phenyl-1,2,4-triazolo[4,3-b]pyridazine (100 mg, 0.35 mmol) and N-methyl-N-(1-methyl-1H-1,2,4-triazol-3-ylmethyl)amine (150 mg, 1.2 mmol) in triethylamine (1 ml) and dry DMF (1 ml) was stirred and heated at 100° C. in a sealed tube for 16 hours. Upon cooling the volatiles were removed in vacuo, and the residue was partitioned between dichloromethane and saturated aqueous sodium hydrogen carbonate. The aqueous was further extracted with dichloromethane (x2). The combined extracts were dried (Na$_2$SO$_4$), filtered and evaporated. The residue was purified by chromatography on silica gel, eluting with 2%→5% methanol-dichloromethane to give the free base as on oil. Treatment with a solution of hydrogen chloride in methanol gave the title compound (40 mg, 30%) as a pale yellow solid. $^1$H NMR (360 MHz, d$_6$-DMSO) δ 1.86–1.92 (1H, m), 1.96–2.04 (1H, m), 2.20–2.32 (2H, m), 2.40–2.46 (2H, m), 2.97 (3H, s), 3.83 (3H, s), 4.42 (2H, s), 7.54–7.60 (3H, m), 8.26 (1H, s), 8.36 (2H, br d, J=8 Hz), 8.48 (1H, s); MS (ES$^+$) m/e 374 [MH]$^+$.

EXAMPLE 3

7-Cyclobutyl-6-(5,6-dihydro-8H-1,2,4-triazolo[1,5-α]pyrazin-7-yl)-3-phenyl-1,2,4-triazolo[4,3-b]pyridazine a) 2-(1,2,4-Triazol-1-yl)ethanol 2-Chloroethanol (50 ml, 0.75 mol) was added to a stirred suspension of 1,2,4-triazole, sodium salt (46 g, 0.5 mol) in dry methanol (300 ml) at room temperature under nitrogen. The mixture was then stirred and heated at reflux for 18 hours. Upon cooling, the reaction was quenched with water (50 ml). The methanol was then removed in vacuo. The residue was diluted with water (approx. 200 ml), and then extracted with ethyl acetate using a continuous extractor for 24 hours. The ethyl acetate was dried (Na$_2$SO$_4$), filtered and evaporated to give the title compound (12.8 g, 23%) as an oil. This material was used without further purification. $^1$H NMR(360 MHz, d$_6$-DMSO) δ 3.72–3.76 (2H, m), 4.19–4.22 (2H, m), 4.94 (1H, t, J=5.4 Hz),7.94 (1H, s), 8.44 (1H, s). MS (ES$^+$) m/e 114 [MH]$^+$.

b) 2-(5-Hydroxymethyl-1,2,4-triazol-1-yl)ethanol

A solution of 2-(1,2,4-triazol-1yl)ethanol (5.0 g, 44 mmol) in 38% w/v aqueous formaldehyde (25 ml) was stirred and heated at 135° C. in a sealed tube for 18 hours. Upon cooling the volatiles were removed in vacuo (azeotroping with ethanol). The residue was purified by chromatography on silica gel, eluting with 5→10→15% methanol-dichloromethane to give the title compound (4.3 g, 68%) as a thick oil. $^1$H NMR (360 MHz, d$_6$-DMSO) δ 3.69–3.74 (2H, m), 4.24 (2H, t, J=5.7 Hz), 4.60 (2H, d, J=5.7 Hz), 4.96 (1H, t, J=5.3 Hz), 5.51 (1H, t, J=5.8 Hz), 7.84 (1H, s); MS (ES$^+$) m/e 144 [MH]$^+$.

c) 5,6,7,8-Tetrahydro-1,2,4-triazolo[1,5-α]pyrazine

Thionyl chloride (20 ml) was added to 2-(5-hydroxymethyl-1,2,4-triazol-1-yl)ethanol (2.0 g, 14 mmol) at 0° C. The mixture was stirred and the cooling bath was removed. The clear solution was then stirred and heated at reflux. After 2 hours the reaction was allowed to cool, and the volatiles were removed in vacuo. The residue was then carefully treated with cold saturated aqueous sodium hydrogen carbonate. The aqueous was extracted with dichloromethane (x3). The combined extracts were dried (Na$_2$SO$_4$), filtered and evaporated to give the bis-chloride (2.5 g) as an oil. This material was used without further purification.

A solution of bis-chloride, from above, in 1,4-dioxane (5 ml) and aqueous ammonia (15 ml) was stirred and heated at 80° C. in a sealed tube for 4 hours. The volatiles were removed in vacuo to give the title compound as the hydrochloride salt (2.1 g, 90%). The free base was obtained after chromatography on silica gel, eluting with dichloromethane-methanol-aqueous ammonia (80:8.1). $^1$H NMR (250 MHz, d$_6$-DMSO) δ 3.1 (1H, br s), 3.34 (2H, t, J=7.8 Hz), 4.13 (2H, s), 4.25 (2H, t, J=7.8 Hz), 8.10 (1H, s); MS (ES$^+$) m/e 125 [MH]$^+$.

d) 7-Cyclobutyl-6-(5,6-dihydro-8H-1,2,4-triazolo[1,5-α]pyrazin-7-yl)-3-phenyl-1,2,4-triazolo[4,3-b]pyridazine A mixture of 6-chloro-7-cyclobutyl-3-phenyl-1,2,4-triazolo[4,3-b]pyridazine (150 mg, 0.53 mmol) and 5,6,7,8-tetrahydro-1,2,4-triazolo[1,5-α]pyrazine (190 mg, 1.53 mmol) in dimethyl sulphoxide (1 ml) was stirred and heated at 150° C. for 20 hours. The mixture was partitioned between dichloromethane and water. The aqueous phase was further extracted with dichloromethane (x2). The combined extracts were dried (Na$_2$SO$_4$), filtered and evaporated. The residue was purified by chromatography on silica gel, eluting with 3→4% methanol-dichloromethane to give the title compound (52 mg, 26%) as an off-white solid (after trituration with diethyl ether). $^1$H NMR (360 MHz, CDCl$_3$) δ 2.00–2.28 (4H, m), 2.48–2.55 (2H, m), 3.68–3.80 (3H, m), 4.43 (2H, t, J=5.5 Hz), 4.67 (2H, s), 7.46–7.56 (3H, m), 7.97 (1H, s), 8.09 (1H, s),8.37 (2H, br d, J=8 Hz); MS (ES$^+$) m/e 373 [MH]$^+$.

EXAMPLE 4

7-Cyclobutyl-3-phenyl-1,2,4-triazolo[4,3-b]pyridazin-6-ylamine

6-Chloro-7-cyclobutyl-3-phenyl-1,2,4-triazolo[4,3-b]pyridazine (200 mg, 0.70 mmol) was suspended in methanol (8 ml). The mixture was saturated with ammonia and heated in a sealed tube at 50° C. overnight. The mixture was evaporated in vacuo, triturated (diethyl ether/hexane) and dried to give the title compound $^1$H NMR (360 MHz, d$_6$-DMSO) δ 1.82–1.87 (1H, m), 1.99–2.35 (5H, m), 3.54–3.64 (1H, m), 7.34 (2H, vbs), 7.48–7.62 (3H, m), 8.08 (1H, s), 8.41 (2H, d, J=7.1 Hz); MS (ES$^+$) m/e 266 [MH]$^+$.

EXAMPLE 5

N-(7-Cyclobutyl-3-phenyl-1,2,4-triazolo[4,3-b]pyridazin-6-yl)-N-methylamine

The title compound was prepared using an analogous procedure to that described in Example 4. MS (ES$^+$) m/e 280 [MH]$^+$.

EXAMPLE 6

7-Cyclobutyl-6-(morpholin-4yl)-3-phenyl-1,2,4-triazolo[4,3-b]pyridazine

6-Chloro-7-cyclobutyl-3-phenyl-1,2,4-triazolo[4,3-b]pyridazine (100 mg, 0.35 mmol), morpholine (154 mg, 1.8 mmol) and triethylamine (178 mg, 1.8 mmol) were heated in 1,4 dioxane (6 ml) in a sealed tube at 90° C. for 24 h. The reaction mixture was partitioned (ethyl acetate/water). The organic layer was washed (water, brine), dried (MgSO$_4$) and was evaporated in vacuo. The residue was purified by chromatography on silica gel, eluting with ethyl acetate to give the title compound. $^1$H NMR (250 MHz, CDCl$_3$) δ 1.96–2.88 (1H, m), 2.48 (2H, m), 3.25–3.28 (4H, m), 3.70–3.76 (1H, m), 3.90–3.94 (4H, m), 7.52–7.55 (3H, m), 7.98 (1H, s), 8.49 (2H, s); MS (ES$^+$) m/e 336 [MH]$^+$.

EXAMPLE 7

N-(7-Cyclobutyl-3-phenyl-1,2,4-triazolo[4,3-b] pyridazin-6-yl)-N-(2-methoxethyl)amine The title compound was prepared using an analogous procedure to that described in Example 6. $^1$H NMR (360 MHz, CDCl$_3$) δ 1.97 (1H, m), 2.20–2.25 (3H, m), 2.44–2.46 (2H, m), 3.41 (4H, s), 3.64–3.70 (4H, m), 4.88 (1H, bs), 7.43–7.53 (3H, m), 7.65 (1H, s), 8.51 (2H, d, J=7.0 Hz).

EXAMPLE 8

N-(7-Cyclobutyl-3-phenyl-1,2,4-triazolo[4,3-b] pyridazin-6-yl)-N-(pyridin-2-ylmethyl)amine The title compound was prepared using an analogous procedure to that described in Example 6. $^1$H NMR (250 MHz, CDCl$_3$) δ 2.00–2.05 (1H, m), 2.25–2.31 (3H, m), 2.55–2.61 (2H, m), 3.55–3.61 (1H, sm), 4.73 (2H, d, J=4.2 Hz), 6.40 (1H, vbs), 7.24–7.29 (1H, m), 7.35–7.58 (4H, m), 7.68–7.76 (2H, m), 8.50–8.68 (3H, m); MS (ES$^+$) m/e 357 [MH]$^+$.

EXAMPLE 9

N'-(7-Cyclobutyl-3-phenyl-1,2,4-triazolo[4,3-b] pyridazin-6-yl)-N,N-dimethylethane-1,2-diamine 6-Chloro-7-cyclobutyl-3-phenyl-1,2,4-triazolo[4,3-b] pyridazine (100 mg, 0.35 mmol) and N,N-dimethylethylenediamine were heated together in a sealed tube at 60° C. for 24 h. The mixture was cooled and the white precipitate was collected by filtration and washed with diethyl ether, then dried to give the title compound. $^1$H NMR (250 MHz, CDCl$_3$) δ 1.94 (1H, m), 2.12–2.24 (3H, m), 2.29 (6H, s), 2.41–2.50 (2H, m), 2.59–2.64 (2H, m), 3.38–3.49 (3H, m), 5.51 (1H, vbs), 7.41–7.52 (3H, m), 7.62 (1H, m), 8.54–8.62 (2H, m); MS (ES$^+$) m/e 337 [MH]$^+$.

EXAMPLE 10

N-(7-Cyclobutyl-3-phenyl-1,2,4-triazolo[4,3-b] pyridazin-6-yl)-N-[3-(morpholin-4-yl)propyl]amine The title compound was prepared using an analogous procedure to that described in Example 9. $^1$H NMR (250 MHz, d$_6$-DMSO) δ 1.48–2.42 (12H, m), 3.49–3.57 (9H, m), 6.70 (1H, m), 7.49–7.60 (3H, m), 7.82 (1H, s), 8.45–8.48 (2H, m); MS (ES$^+$) m/e 393 [MH]$^+$.

EXAMPLE 11

(±)-N-(7-Cyclobutyl-3-phenyl-1,2,4-triazolo[4,3-b] pyridazin-6-yl)-N-[2-(1-(methylpyrrolidin-2-yl) ethyl]amine The title compound was prepared using an analogous procedure to that described in Example 9. $^1$H NMR (250 MHz, d$_6$-DMSO) δ 1.55–2.18 (12H, m), 2.24 (3H, s), 2.38 (2H, m), 2.95 (1H, m), 3.40–3.49 (3H, m), 6.96 (1H, m), 7.49–7.58 (3H, m), 7.82 (1H, s), 8.46–8.52 (2H, m); MS (ES$^+$) m/e 377 [MH]$^+$.

EXAMPLE 12

N'-(7-Cyclobutyl-3-phenyl-1,2,4-triazolo[4,3-b] pyridazin-6-yl)-N,N-dimethylpropane-1,3-diamine The title compound was prepared using an analogous procedure to that described in Example 9. $^1$H NMR (250 MHz, CDCl$_3$) δ 1.82–2.03 (2H, m), 2.06–2.23 (2H, m), 2.34 (6H, s), 2.40–2.57 (4H, m), 3.21–3.31 (1H, m), 3.51–3.58 (2H, m), 7.16 (1H, vbs), 7.40–7.55 (3H, m), 7.63 (1H, m), 8.52–8.62 (2H, m); MS (ES$^+$) m/e 351 [MH]$^+$.

EXAMPLE 13

N-(7-Cyclobutyl-3-phenyl-1,2,4-triazolo[4,3-b] pyridazin-6-yl)-N-[3-(imidazol-1-yl)propyl]amine The title compound was prepared using an analogous procedure to that described in Example 9. MS (ES$^+$) m/e 374 [MH]$^+$.

EXAMPLE 14

N-(7-Cyclobutyl-3-phenyl-1,2,4-triazolo[4,3-b] pyridazin-6-yl)-N-[3-(pyrrolidin-1-yl)propyl]amine The title compound was prepared using an analogous procedure to that described in Example 9. MS (ES$^+$) m/e 377 [MH]$^+$.

EXAMPLE 15

1-[3-(7-Cyclobutyl-3-phenyl-1,2,4-triazolo[4,3-b] pyridazin-6-ylamino)-propyl]pyrrolidin-2-one The title compound was prepared using an analogous procedure to that described in Example 9. MS (ES$^+$) m/e 391 [MH]$^+$.

EXAMPLE 16

N-(7-Cyclobutyl-3-phenyl-1,2,4-triazolo[4,3-b] pyridazin-6-yl)-N-[2-(piperazin-1-yl)ethyl]amine The title compound was prepared using an analogous procedure to that described in Example 9. MS (ES$^+$) m/e 378 [MH]$^+$.

EXAMPLE 17

N-(7-Cyclobutyl-3-phenyl-1,2,4-triazolo[4,3-b] pyridazin-6-yl)-N-[2-(morpholin-4-yl)ethyl]amine The title compound was prepared using an analogous procedure to that described in Example 9. MS (ES$^+$) m/e 379 [MH]$^+$.

EXAMPLE 18

N-(7-Cyclobutyl-3-phenyl-1,2,4-triazolo[4,3-b] pyridazin-6-yl)-N-[2-(pyridin-2-yl)ethyl]amine The title compound was prepared using an analogous procedure to that described in Example 9. MS (ES$^+$) m/e 371 [MH]$^+$.

What is claimed is:

1. A compound of formula I, or a salt thereof:

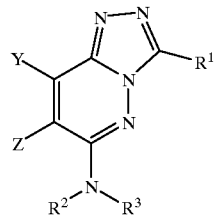

(I)

wherein

Y represents hydrogen or $C_{1-6}$alkyl;

Z represents $C_{1-6}$alkyl, $C_{3-7}$cycloalkyl, $C_{4-7}$cycloalkenyl, aryl, or di($C_{1-6}$)alkylamino, any of which groups may be optionally substituted by one or two substituents independently being $C_{1-6}$alkyl, phenyl($C_{1-6}$)alkyl, naphthyl($C_{1-6}$)alkyl, pyridyl($C_{1-6}$)alkyl, halogen, halo($C_{1-6}$)alkyl, cyano, cyano($C_{1-6}$)alkyl, oxo, hydroxy, hydroxymethyl, $C_{1-6}$alkoxy, $C_{3-7}$cycloalkyl($C_{1-6}$)alkoxy, $C_{3-7}$cycloalkoxy, amino, $C_{1-6}$alkylamino, di($C_{1-6}$)alkylamino, amino($C_{1-6}$)alkyl, di($C_{1-6}$)alkylamino($C_{1-6}$)alkyl, di($C_{1-6}$)alkylaminocarbonyl($C_{1-6}$)alkyl, N-($C_{1-6}$)alkylpiperidinyl, pyrrolidinyl($C_{1-6}$)alkyl, piperazinyl($C_{1-6}$)alkyl, morpholinyl($C_{1-6}$)alkyl, di($C_{1-6}$)alkylmorpholinyl($C_{1-6}$)alkyl or imidazolyl($C_{1-6}$)alkyl;

$R^1$ represents $C_{3-7}$cycloalkyl, phenyl, furyl, thienyl or pyridinyl, any of which groups may be optionally substituted by one or two substituents independently being $C_{1-6}$alkyl, phenyl($C_{1-6}$)alkyl, naphthyl($C_{1-6}$)alkyl, pyridyl($C_{1-6}$)alkyl, halogen, halo($C_{1-6}$)alkyl, cyano, cyano($C_{1-6}$)alkyl, oxo, hydroxy, hydroxymethyl, $C_{1-6}$alkoxy, $C_{3-7}$cycloalkyl($C_{1-6}$)alkoxy, $C_{3-7}$cycloalkoxy, amino, $C_{1-6}$alkylamino, di($C_{1-6}$)alkylamino, amino($C_{1-6}$)alkyl, di($C_{1-6}$)alkylamino($C_{1-6}$)alkyl, di($C_{1-6}$)alkylaminocarbonyl($C_{1-6}$)alkyl, N-($C_{1-6}$)alkylpiperidinyl, pyrrolidinyl($C_{1-6}$)alkyl, piperazinyl($C_{1-6}$)alkyl, morpholinyl($C_{1-6}$)alkyl, di($C_{1-6}$)alkylmorpholinyl($C_{1-6}$)alkyl or imidazolyl($C_{1-6}$)alkyl;

$R^2$ represents hydrogen or $C_{1-6}$alkyl; and $R^3$ represents hydrogen or $C_{1-6}$alkyl, $C_{3-7}$cycloalkyl($C_{1-6}$)alkyl, propargyl, aryl($C_{1-6}$)alkyl, azetidinyl($C_{1-6}$)alkyl, pyrrolidinyl($C_{1-6}$)alkyl, piperidinyl($C_{1-6}$)alkyl, piperazinyl($C_{1-6}$)alkyl, morpholinyl($C_{1-6}$)alkyl, thiomorpholinyl($C_{1-6}$)alkyl, pyridyl($C_{1-6}$)alkyl, quinolinyl($C_{1-6}$)alkyl, isoquinolinyl($C_{1-6}$)alkyl, pyridazinyl($C_{1-6}$)alkyl, pyrimidinyl($C_{1-6}$)alkyl, pyrazinyl($C_{1-6}$)alkyl, quinoxalinyl($C_{1-6}$)alkyl, furyl($C_{1-6}$)alkyl, benzofuryl($C_{1-6}$)alkyl, dibenzofuryl($C_{1-6}$)alkyl, thienyl($C_{1-6}$)alkyl, benzthienyl($C_{1-6}$)alkyl, pyrrolyl($C_{1-6}$)alkyl, indolyl($C_{1-6}$)alkyl, pyrazolyl($C_{1-6}$)alkyl, indazolyl($C_{1-6}$)alkyl, oxazolyl($C_{1-6}$)alkyl, isoxazolyl($C_{1-6}$)alkyl, thiazolyl($C_{1-6}$)alkyl, isothiazolyl($C_{1-6}$)alkyl, imidazolyl($C_{1-6}$)alkyl, benzimidazolyl($C_{1-6}$)alkyl, oxadiazolyl($C_{1-6}$)alkyl, thiadiazolyl($C_{1-6}$)alkyl, triazolyl($C_{1-6}$)alkyl, or tetrazolyl($C_{1-6}$)alkyl, any of which groups may be optionally substituted by one or two substituents independently being $C_{1-6}$alkyl, phenyl($C_{1-6}$)alkyl, naphthyl($C_{1-6}$)alkyl, pyridyl($C_{1-6}$)alkyl, halogen, halo($C_{1-6}$)alkyl, cyano, cyano($C_{1-6}$)alkyl, oxo, hydroxy, hydroxymethyl, $C_{1-6}$alkoxy, $C_{3-7}$cycloalkyl($C_{1-6}$)alkoxy, $C_{3-7}$cycloalkoxy, amino, $C_{1-6}$alkylamino, di($C_{1-6}$)alkylamino, amino($C_{1-6}$)alkyl, di($C_{1-6}$)alkylamino($C_{1-6}$)alkyl, di($C_{1-6}$)alkylaminocarbonyl($C_{1-6}$)alkyl, N-($C_{1-6}$)alkylpiperidinyl, pyrrolidinyl($C_{1-6}$)alkyl, piperazinyl($C_{1-6}$)alkyl, morpholinyl($C_{1-6}$)alkyl, di($C_{1-6}$)alkylmorpholinyl($C_{1-6}$)alkyl or imidazolyl($C_{1-6}$)alkyl.

2. A compound as claimed in claim 1, represented by formula IIA, or a salt thereof:

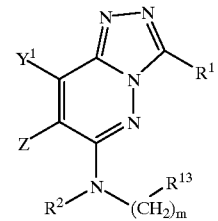

(IIA)

wherein $Y^1$ represents hydrogen or methyl;

Z, $R^1$ and $R^2$ are defined as in claim 1;

m is 1, 2 or 3; and $R^{13}$ represents phenyl, naphthyl, pyridinyl, quinolinyl, isoquinolinyl, pyridazinyl, pyrimidinyl, pryazinyl, quinoxalinyl, furyl, banzofuryl, dibenzofuryl, thienyl, benzthienyl, pyrrolyl, indolyl, pyrazolyl, indazolyl, oxazolyl, isoxazolyl, thiazolyl, isothiazolyl, imidazolyl, benzimidazolyl, oxadiazolyl, thiadiazolyl, triazolyl, or tetrazolyl, any of which groups may be optionally substituted by one or two substituents independently being $C_{1-6}$alkyl, phenyl($C_{1-6}$)alkyl, naphthyl($C_{1-6}$)alkyl, pyridyl($C_{1-6}$)alkyl, halogen, cyano, cyano($C_{1-6}$)alkyl, hydroxymethyl, $C_{1-6}$alkoxy, $C_{3-7}$cycloalkyl($C_{1-6}$)alkoxy, amino($C_{1-6}$)alkyl, di($C_{1-6}$)alkylamino($C_{1-6}$)alkyl, di($C_{1-6}$)alkylaminocarbonyl($C_{1-6}$)alkyl, N-($C_{1-6}$)alkylpiperidinyl, pyrrolidinyl($C_{1-6}$)alkyl, piperazinyl($C_{1-6}$)alkyl, morpholinyl($C_{1-6}$)alkyl.

3. A compound as claimed in claim 2 represented by formula IIB, or a pharmaceutically acceptable salt thereof:

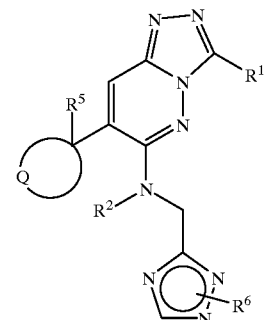

(IIB)

wherein

Q represents a cyclopropyl, cyclobutyl, cyclopentyl or cyclohexyl ring;

$R^5$ represents hydrogen or methyl; and $R^6$ represents hydrogen or methyl.

4. A compound selected from:

N-(7-cyclobutyl-3-phenyl-1,2,4-triazolo[4,3-b]pyridazin-6-yl)-N-(1-methyl-1H-1,2,4-triazol-3-ylmethyl)amine;

N-(7-cyclobutyl-3-phenyl-1,2,4-triazolo[4,3-b]pyridazin-6-yl)-N,N-dimethylamine;

N-(7-cyclobutyl-3-phenyl-1,2,4-triazolo[4,3-b]pyridazin-6-yl)-N-methyl-N-(1-methyl-1H-1,2,4-triazol-3-ylmethyl)amine;

7-cyclobutyl-3-phenyl-1,2,4-triazolo[4,3-b]pyridazin-6-ylamine;

N-(7-cyclobutyl-3-phenyl-1,2,4-triazolo[4,3-b]pyridazin-6-yl)-N-methylamine;

N-(7-cyclobutyl-3-phenyl-1,2,4-triazolo[4,3-b]pyradazin-6-yl)-N-(pyridin-2-methoxethyl)amine;

N-(7-cyclobutyl-3-phenyl-1,2,4-triazolo[4,3-b]pyridazin-6-yl)-N-(pyridin-2-ylmethyl)amine;

N-(7-cyclobutyl-3-phenyl-1,2,4-triazolo[4,3-b]pyridazin-6-yl)-N,N-dimethylethane-1,2-diamine;

N-(7-cyclobutyl-3-phenyl-1,2,4-triazolo[4,3-b]pyridazin-6-yl)-N-[3-(morpholin-4-yl)propyl]amine;

(±)-N-(7-cyclobutyl-3-phenyl-1,2,4-triazolo[4,3-b]pyridazin-6-yl)-N-[2-(1-methylpyrrolidin-2-yl)ethyl]amine;

N'-(7-cyclobutyl-3-phenyl-1,2,4-triazolo[4,3-b]pyridazin-6-yl)-N,N-dimethylpropane-1,3-diamine;

N-(7-cyclobutyl-3-phenyl-1,2,4-triazolo[4,3-b]pyridazin-6-yl)-N-[3-(imidazol-1-yl)propyl]amine;

N-(7-cyclobutyl-3-phenyl-1,2,4-triazolo[4,3-b]pyridazin-6-yl)-N-[3-pyrrolidin-1-yl)propyl]amine;

1-[3-(7-cyclobutyl-3-phenyl-1,2,4-triazolo[4,3-b]pyridazin-6-ylamino)-propyl]pyrrolidin-2-one;

N-(7-cyclobutyl-3-phenyl-1,2,4-triazolo[4,3-b]pyridazin-6-yl)-N-[2-(piperazin-1-yl)ethyl]amine;

N-(7-cyclobutyl-3-phenyl-1,2,4-triazolo[4,3-b]pyridazin-6-yl)-N-[2-(morpholin-4-yl)ethyl]amine; or N-(7-cyclobutyl-3-phenyl-1,2,4-triazolo[4,3-b]pyridazin-6-yl)-N-[2-(pyridin-2-yl)ethyl]amine;

or a pharmaceutically acceptable salt thereof.

5. A pharmaceutical composition comprising a compound of formula I as defined in claim 1 or a pharmaceutically acceptable salt thereof in association with a pharmaceutically acceptable carrier.

6. A process for the preparation of a compound as claimed in claim 1, which comprises:

(A) reacting a compound of formula III with a compound of formula IV:

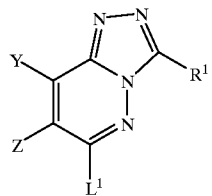

(III)

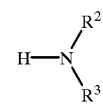

(IV)

wherein Y, Z, $R^1$, $R^2$ and $R^3$ are as defined in claim 1, and $L^1$ represents a suitable leaving group; or (B) reacting a compound of formula Z—$CO_2H$ with a compound of formula VII:

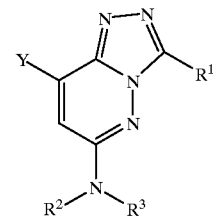

(VII)

wherein Y, Z, $R^1$, $R^2$ and $R^3$ are as defined in claim 1; in the presence of silver nitrate and ammonium persulphate; or (C) reacting a compound of formula VIII with a compound of formula IX:

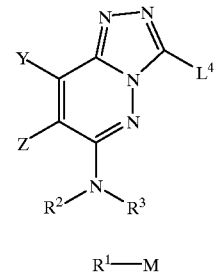

(VIII)

$R^1$—M (IX)

wherein Y, Z, $R^1$, $R^2$ and $R^3$ are as defined in claim 1, M represents —B(OH)$_2$ or —Sn(Alk)$_3$ in which Alk represents a $C_{1-6}$alkyl group, and $L^4$ represents a suitable leaving group; in the presence of a transition metal catalyst; and (D) subsequently, if desired, converting a compound of formula I initially obtained into a further compound of formula I by standard methods.

7. A method for the treatment and/or prevention of anxiety which comprises administering to a patient in need of such treatment an effective amount of a compound of formula I as defined in claim 1, or a pharmaceutically acceptable salt thereof.

8. A method for the treatment and/or prevention of convulsions which comprises administering to a patient in need of such treatment an effective amount of a compound of formula I as defined in claim 1, or a pharmaceutically acceptable salt thereof.

\* \* \* \* \*